United States Patent
Bland et al.

[11] Patent Number: 6,114,313
[45] Date of Patent: Sep. 5, 2000

[54] PHARMACEUTICAL COMPOSITIONS FOR FREEZE DRYING

[75] Inventors: Chris Bland; Gerald Steele, both of Leics, United Kingdom

[73] Assignee: Astra Zeneca UK Limited, London, United Kingdom

[21] Appl. No.: 09/043,159
[22] PCT Filed: Dec. 11, 1997
[86] PCT No.: PCT/SE97/02068
  § 371 Date: Mar. 13, 1998
  § 102(e) Date: Mar. 13, 1998
[87] PCT Pub. No.: WO98/28009
  PCT Pub. Date: Jul. 2, 1998

[30] Foreign Application Priority Data
Dec. 20, 1996 [SE] Sweden ................................. 9604795

[51] Int. Cl.[7] ..................................... A61K 31/70
[52] U.S. Cl. .................................. 514/47; 514/25; 514/48; 514/53; 514/951
[58] Field of Search ................................. 514/25, 47, 48, 514/53, 951

[56] References Cited

FOREIGN PATENT DOCUMENTS

| 383569 | 8/1990 | European Pat. Off. . |
| 520748 | 12/1992 | European Pat. Off. . |
| 0619119 | 10/1994 | European Pat. Off. ....... A61K 37/24 |
| 2423811 | 12/1974 | Germany . |
| 1228915 | 9/1989 | Japan .............................. A61K 31/70 |
| 91/18091 | 11/1991 | WIPO . |

*Primary Examiner*—James O. Wilson
*Attorney, Agent, or Firm*—Nixon & Vanderhye

[57] ABSTRACT

A pharmaceutical composition comprising a nucleotide analogue, mannitol and a modifying additive which is sodium chloride or a polyol which is suitable for freeze drying.

13 Claims, No Drawings

PHARMACEUTICAL COMPOSITIONS FOR FREEZE DRYING

The present invention provides a pharmaceutical composition suitable for freeze-drying and a process for the preparation of the composition.

BACKGROUND OF THE INVENTION

Freeze drying is a well known process used to prepare storage stable formulations of pharmaceutical compounds which otherwise suffer degradation when stored in the presence of water, for example, because of disproportionation and/or hydrolysis. A typical freeze drying cycle consists of four stages. Freezing the composition of the compound to be freeze dried, a primary drying cycle which comprises applying a vacuum and sufficient heat to sublimate the ice present in the composition, a second drying cycle which removes any residual water and then recovery of the freeze dried composition. It is an expensive process because it takes a long time and because a low temperature and a vacuum are required. A low temperature is required because the vacuum needs to be applied at a temperature below the eutectic temperature for mixtures of crystalline substances or below the glass transition or collapse temperature for amorphous mixtures. This is to ensure that the water present is vapourised without passing through the liquid state and so that the amorphous mixtures do not collapse. A collapsed amorphous mixture is effectively useless because it is very difficult to reconstitute and may be unstable.

To keep costs down it is preferable for the collapse or eutectic temperature not to be too low in order that the cooling cost is reduced. A higher collapse or eutectic temperature is also advantageous because the evaporation is hastened which reduces the length of time the vacuum is needed. Compositions suitable for freeze drying have been sought which produce a stable product and for which the collapse or eutectic temperature is not too low.

DESCRIPTION OF THE INVENTION

According to a first aspect of the invention there is provided a pharmaceutical composition comprising a nucleotide analogue, mannitol and a modifying additive which is sodium chloride or a polyol.

The invention further provides a pharmaceutical composition in freeze dried, spray dried or vacuum dried form and in reconstituted form.

According to the invention there is further provided a process for the preparation of a composition according to the invention which comprises mixing the ingredients of the composition, and either freezing them and drying the frozen mixture, or spraying them (for example into warm air).

The use of the combination of mannitol and the modifying additive in the compositions of the invention has unexpectedly been found to improve the compositions long term stability after freeze drying. Another advantage of using such a combination is that vial breakage or cracking during freeze-drying is prevented.

A nucleotide is a compound comprising a purine or pyrimidine base attached to a pentosugar wherein one or more of the hydroxy groups of the pentosugar are phosphorylated by a mono- or polyphosphate. A nucleotide analogue for use in the invention is in general a compound in which one or more of the three moieties of which a nucleotide is comprised is modified, for example, by attachment of one or more substituents and/or by replacement of one or more of the skeletal atoms.

The nucleotide used in the invention is preferably a nucleotide from WO 94/18216, that is to say a compound of formula (I):

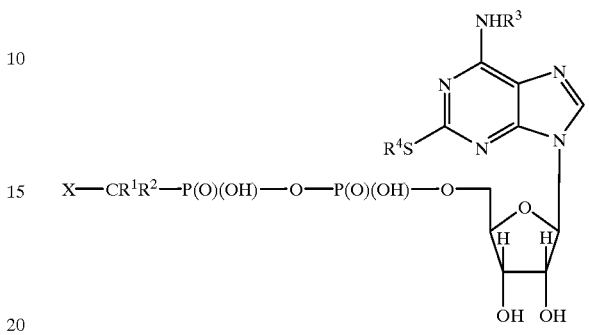

wherein $R^1$ and $R^2$ independently represent hydrogen or halogen, $R^3$ and $R^4$ independently represent phenyl, or $C_{1-6}$-alkyl optionally substituted by one or more substituents selected from $OR^5$, $C_{1-6}$-alkylthio, $NR^6R^7$, phenyl, $COOR^8$ and halogen, $R^5$, $R^6$, $R^7$ and $R^8$ independently represent hydrogen or $C_{1-6}$-alkyl, and X represents an acidic moiety, or a pharmaceutically acceptable salt thereof.

Compounds of formula (I) may exist in tautomeric, enantiomeric and diastereomeric forms, all of which are included within the scope of the definition.

Pharmaceutically acceptable salts of the compounds of formula (I) include alkali metal salts, e.g. sodium and potassium salts; alkaline earth metal salts, e.g. calcium and magnesium salts; salts of the Group III elements, e.g. aluminium salts; and ammonium salts. Salts with suitable organic bases, for example, salts with hydroxylamine; lower alkylamines, e.g. methylamine or ethylamine; with substituted lower alkylamines, e.g. hydroxysubstituted alkylamines; or with monocyclic nitrogen heterocyclic compounds, e.g. piperidine or morpholine; and salts with amino acids, e.g. with arginine, lysine etc., or an N-alkyl derivative thereof; or with an aminosugar, e.g. N-methyl-D-glucamine or glucosamine. The non-toxic physiologically acceptable salts are preferred, although other salts are also useful, e.g. in isolating or purifying the product.

Alkyl groups in the definitions of compounds of formula (I) include straight, branched or cyclic, saturated or unsaturated alkyl groups. Aryl groups in the definitions of compounds of formula (I) include both carbocyclic and heterocyclic groups. The groups may contain rings or various numbers of C-atoms and may be fused ring structures. Particular carbocyclic aryl groups which may be mentioned are phenyl and naphthyl. Heteroaryl groups include nitrogen, oxygen or sulphur heterocycles and may contain one or more heteroatoms. Examples of heterocycles containing only one heteroatom include pyrrole, furan, thiophen and pyridine. Groups containing more than one heteroatom include pyrazole, oxazole, thiazole, triazole, oxadiazole, thiadiazole etc.

Halogens which $R^1$ and $R^2$ may represent include F, Cl, Br and I. Preferably $R^1$ and $R^2$ are the same and more preferably represent Cl.

Preferably $R^3$ and $R^4$ represent $C_{1-6}$-alkyl optionally substituted by one or more substituents selected from $OR^5$, $C_{1-6}$-alkylthio, $NR^6R^7$, phenyl, $COOR^8$ and halogen. Halogens with which $R^3$ and $R^4$ may be substituted include Cl, Br and I, and especially F.

Particularly preferred are compounds in which $R^3$ represents $C_{1-6}$-alkyl optionally substituted by $C_{1-6}$-alkylthio. Particular alkyl groups that $R^3$ may represent include propyl and butyl, and especially ethyl. Particular substituted alkyl groups that $R^3$ may represent include 2-(methylthio)ethyl.

Preferably $R^4$ represents $C_{1-6}$-alkyl optionally substituted by one or more, e.g. three, halogen atoms. Particular groups that $R^4$ may represent include propyl and 3,3,3-trifluoropropyl.

Acidic moieties which X may represent include Bronsted-Lowry acids, i.e. moieties which act as proton donors. The acidic moiety may be mono- or poly-acidic. Specific acidic moieties which may be mentioned include —$P(O)(OH)_2$, —$SO_3H$ and —$CO_2H$. Preferably X represents —$P(O)(OH)_2$.

Most preferably, the nucleotide analogue is N-[2-(methylthio)ethyl]-2-[(3,3,3-trifluoropropyl)thio]-5'-adenylic acid, monoanhydride with dichloromethylenebisphosphonic acid or a pharmaceutically acceptable salt thereof, that is to say a compound of formula (Ia):

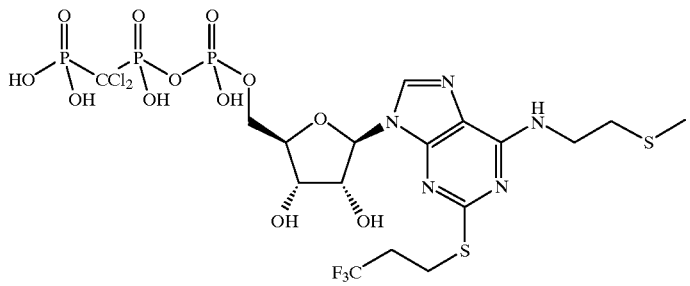

(Ia)

Most preferably the compounds of formula (Ia) is in the form of the tetrasodium salt.

Compounds of formula (I) may be prepared using the methods disclosed in WO 94/18216. The compounds of formula (I) are useful because they exhibit pharmacological activity in mammals. In a further aspect the invention provides a composition as defined herein for use in therapy, in particular, in the prevention of platelet aggregation. The compositions of the invention therefore act as anti-thrombotic agents.

In a further aspect the invention provides a method of treating a platelet aggregation disorder which method comprises treating a subject suffering from a said disorder with a therapeutically effective amount of a pharmaceutical composition as defined herein.

In a still further aspect the invention provides use of a pharmaceutical composition as defined herein in the manufacture of a medicament for treating a platelet aggregation disorder.

The modifying additive or agent is preferably a suitable polyol. This is because when NaCl is used as the modifying agent, the profile of impurities is unfavourable.

A polyol suitable for use in the invention is in general a straight chain polyhydric alcohol or a cyclic molecule comprising one or more keto or aldehyde groups which is preferably a carbohydrate. The polyol used in the composition according to the invention is preferably sorbitol, lactose, sucrose, inositol or trehalose. More preferably the modifying agent is sorbitol because it has surprisingly been found that the long term stability of freeze dried compositions comprising sorbitol is improved compared to such compositions containing other modifying agents.

The composition according to the invention preferably comprises mannitol as a crystallising agent. Suitably the compositions of the invention comprise about 1% or more by weight of mannitol, for example 20–40%. However there is a problem with mannitol in that on freeze drying, the vials containing the mixture without the modifying additive tend to crack due to an amorphous to crystalline phase transition. The amount of the modifying additive is preferably sufficient to prevent this phase transition from occurring, for example about 3 to 25%. A suitable amount can easily be determined by conventional analytical techniques such as differential scanning calorimetry. However the amount of the modifying agent should not be so much as to cause collapse of the composition.

The water content of the formulation is preferably less than 5% by weight, more preferably less than 2% by weight and most preferably less than 1% by weight.

The pharmaceutical composition according to the present invention optionally additionally comprises a pharmaceutically acceptable excipient, for example a chelating or sequestering agent, an antioxidant, a tonicity adjusting agent, a pH modifying agent and/or a buffering agent, for example one or more of those disclosed in "Review of Excipients and pH's for Parenteral Products used in the United States" Yu-Chang John Wang and R R Kowal, J Parenteral Drug Association, 34, 452–462 (1980).

The process for preparing the pharmaceutical composition according to the present invention is suitably carried out using any lyophilisation, vacuum drying or spray drying technique commonly used within the pharmaceutical area. In a further aspect the invention provides a process for preparing a pharmaceutical composition as defined herein which comprises mixing a nucleotide analogue, mannitol and a sodium chloride or polyol modifying additive and subjecting the mixture to a lyophilisation, vacuum drying or spray drying procedure.

A preferred process according to the invention is a vial freeze-drying process. Such a process comprises filling sterile vials with a sterile filtered solution of the composition according to the invention. A sterile freeze-drying stopper is partially inserted into the vial which is frozen, e.g. at a temperature from −30 to 40° C., and thereafter vacuum dried in the frozen state. After drying the stopper is fully inserted before removing the vial from the lyophilization unit.

Upon use but before administration, the pharmaceutical compositions according to the present invention are generally reconstituted in a pharmaceutically acceptable diluent. Examples of pharmaceutically acceptable diluents include water, saline and dextrose. Preferably water is used as the diluent. In a further aspect the invention provides a process for preparing a pharmaceutical composition as defined herein which comprises mixing a nucleotide analogue, mannitol and a sodium chloride or polyol modifying additive with a pharmaceutically acceptable diluent.

Suitably a solution of the pharmaceutical composition according to the invention obtained after reconstitution and containing mannitol is an isotonic solution.

In a preferred embodiment the pH of the composition of the present invention is from about 6 to about 10, more preferably from about 7 to about 9.

The pharmaceutical composition according to the present invention when reconstituted is preferably administered by injection intravenously, subcutaneously or intramuscularly, preferably intravenously.

The compositions according to the invention may be packed in suitably adapted pharmaceutical application devices, for example syringes, vials or ampoules, such that the addition of water allows the in situ preparation of an aqueous solution of the active ingredient in a form suitable for immediate adminstration to the patient. Such devices form a further aspect of the invention.

EXAMPLES

The invention will now be described in more detail by the following examples.

Example 1

The freeze dried compositions listed in Table 1 were prepared as follows. For each batch 5 ml aliquots of the solution shown were filled into vials and then placed in a Secfroid Lyolab G freeze drier. They were frozen to −35° C., subjected to 2 hours primary drying at −30° C., followed by 33 hours of primary drying during which the temperature was ramped to 35° C. and then 12 hours secondary drying at 35° C. The vacuum was held at 100 mTorr throughout primary and secondary drying.

TABLE 1

| Batch | Component | Amount/ % by wt | Batch | Component | Amount/ % by wt |
|---|---|---|---|---|---|
| 1 | Analogue | 2.2 | 2 | Analogue | 2.4 |
|  | Sorbitol | 21.1 |  | NaCl | 1.4 |
|  | Mannitol | 76.6 |  | Mannitol | 96.2 | wherein the analogue is compound of formula (Ia). They were then stored under the conditions shown in Table 2 and suffered the degradation shown by the amount of impurities.

TABLE 2

| Batch | Storage conditions | Storage time | Total Impurities |
|---|---|---|---|
| 1 | −20° C./ambient humidity | 12 | 1.23 |
|  |  | 26 | 1.26 |
| 1 | 4° C./ambient humidity | 4 | 1.51 |
|  |  | 8 | 1.63 |
|  |  | 12 | 1.34 |
|  |  | 26 | 1.36 |
| 1 | 25° C./60% RH | 4 | 1.57 |
|  |  | 8 | 1.75 |
|  |  | 12 | 1.51 |
|  |  | 26 | 1.55 |
| 1 | 40° C./75% RH | 4 | 1.95 |
|  |  | 8 | 2.22 |
|  |  | 12 | 2.44 |
| 2 | −20° C./ambient humidity | 12 | 1.56 |
|  |  | 26 | 1.50 |
| 2 | 4° C./ambient humidity | 4 | 1.40 |
|  |  | 8 | 1.57 |
|  |  | 12 | 1.54 |
|  |  | 26 | 1.47 |

TABLE 2-continued

| Batch | Storage conditions | Storage time | Total Impurities |
|---|---|---|---|
| 2 | 25° C./60% RH | 4 | 1.44 |
|  |  | 8 | 1.55 |
|  |  | 12 | 1.61 |
|  |  | 26 | 1.67 |
| 2 | 40° C./75% RH | 4 | 1.80 |
|  |  | 8 | 2.10 |
|  |  | 12 | 1.95 | wherein the amount of impurities is a percentage by weight and RH means relative humidity.

Example 2

The freeze dried compositions listed in Table 3 were prepared as follows. For each batch 3 ml aliquots of the solution shown were filled into vials and then placed in a Virtis Genesis 25EL freeze drier. They were frozen to −35° C., subjected to 2 hours primary drying at −30° C., followed by 25–28 hours of primary drying at 5° C. and then 11 hours secondary drying at 35° C. The vacuum was held at 100 mTorr throughout primary and secondary drying.

TABLE 3

| Batch | Component | Amount/ % by wt | Batch | Component | Amount/ % by wt |
|---|---|---|---|---|---|
| 3 | Analogue | 21 | 8 | Analogue | 38.3 |
|  | Sorbitol | 19.8 |  | Sorbitol | 12 |
|  | Mannitol | 59.2 |  | Mannitol | 49.7 |
| 4 | Analogue | 20.9 | 9 | Analogue | 37.1 |
|  | Inositol | 20.4 |  | Sucrose | 6.1 |
|  | Mannitol | 58.7 |  | Mannitol | 56.8 |
| 5 | Analogue | 18.8 | 10 | Analogue | 35.1 |
|  | Sucrose | 22.6 |  | Sorbitol | 18.1 |
|  | Mannitol | 58.6 |  | Mannitol | 46.8 |
| 6 | Analogue | 18.8 | 11 | Analogue | 48.2 |
|  | Trehalose | 22.6 |  | Sorbitol | 16.6 |
|  | Mannitol | 58.6 |  | Mannitol | 35.2 |
| 7 | Analogue | 38.3 | 12 | Analogue | 58.9 |
|  | Sorbitol | 3 |  | Sorbitol | 15.2 |
|  | Mannitol | 58.7 |  | Mannitol | 25.9 | wherein the analogue is a compound of formula (Ia).

Each batch was then stored at 40° C. and 75% relative humidity and suffered the degradation shown in Table 4.

TABLE 4

| Batch | Storage time (weeks) | Impurity A | Impurity B | Total Impurities |
|---|---|---|---|---|
| 3 | 0 | <0.05 | 0.06 | 0.63 |
|  | 4 | 0.06 | 0.06 | 0.77 |
|  | 12 | 0.08 | 0.07 | 0.75 |
|  | 26 | 0.12 | 0.08 | 0.76 |
| 4 | 0 | <0.05 | 0.07 | 0.63 |
|  | 4 | 0.07 | 0.09 | 0.83 |
|  | 12 | 0.24 | 0.32 | 1.17 |
|  | 26 | 0.17 | 0.08 | 0.90 |
| 5 | 0 | 0.07 | 0.07 | 0.74 |
|  | 4 | 0.10 | 0.08 | 0.86 |
|  | 12 | 0.14 | 0.07 | 0.82 |
|  | 26 | 0.24 | 0.08 | 0.99 |
| 6 | 0 | <0.05 | 0.06 | 0.69 |
|  | 4 | 0.14 | 0.08 | 1.00 |
|  | 12 | 0.26 | 0.08 | 0.96 |
|  | 26 | 0.46 | 0.10 | 1.15 |
| 7 | 0 | 0.06 | 0.11 | 0.81 |
|  | 4 | 0.16 | 0.16 | 0.89 |
|  | 12 | 0.29 | 0.22 | 1.10 |

TABLE 4-continued

| Batch | Storage time (weeks) | Impurity A | Impurity B | Total Impurities |
|---|---|---|---|---|
| 8 | 0 | <0.05 | 0.09 | 0.68 |
|  | 4 | 0.08 | 0.09 | 0.73 |
|  | 12 | 0.12 | 0.11 | 0.83 |
| 9 | 0 | 0.05 | 0.10 | 0.74 |
|  | 4 | 0.18 | 0.16 | 0.89 |
|  | 12 | 0.30 | 0.18 | 1.02 |
| 10 | 0 | <0.05 | 0.06 | 0.32 |
|  | 4 | 0.05 | 0.07 | 0.39 |
|  | 12 | 0.08 | 0.07 | 0.43 |
| 11 | 0 | <0.05 | 0.06 | 0.32 |
|  | 4 | 0.05 | 0.06 | 0.38 |
|  | 12 | 0.08 | 0.07 | 0.48 |
| 12 | 0 | <0.05 | 0.06 | 0.33 |
|  | 4 | <0.05 | 0.07 | 0.33 |
|  | 12 | 0.05 | 0.06 | 0.38 | wherein the amount of each impurity is a % by weight and impurity A is a compound of formula (Ib) which is

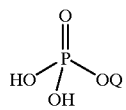

and impurity B is a compound of formula (Ic)

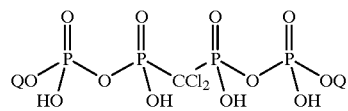

wherein Q represents

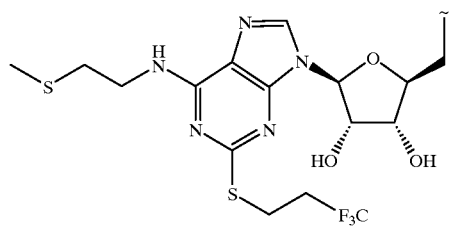

What is claimed is:

1. A pharmaceutical composition comprising a nucleotide analog, mannitol and a modifying additive which is sodium chloride or a polyol, wherein the nucleotide is a compound of formula

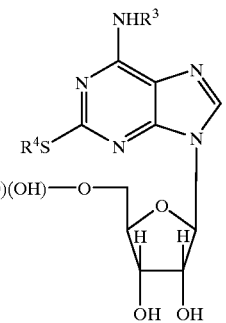

$$X-CR^1R^2-P(O)(OH)-O-P(O)(OH)-O-$$

wherein $R^1$ and $R^2$ independently represent hydrogen or halogen, $R^3$ and $R^4$ independently represent phenyl, or $C_{1-6}$-alkyl optionally substituted by one or more substituents selected from $OR^5$, $C_{1-6}$-alkylthio, $NR^6R^7$, phenyl, $COOR^8$ and halogen, $R^5$, $R^6$, $R^7$ and $R^8$ independently represent hydrogen or $C_{1-6}$-alkyl, and X represents an acidic moiety, or a pharmaceutically acceptable salt thereof.

2. A pharmaceutical composition according to claim 1 in which $R^1$ and $R^2$ are halogen, $R^3$ is $C_{1-6}$-alkyl optionally substituted by $C_{1-6}$-alkylthio, $R^4$ is $C_{1-6}$-alkyl optionally substituted by halogen, and X is —P(O)(OH)$_2$, —SO$_3$H or —CO$_2$H.

3. A pharmaceutical composition according to claim 1 wherein the nucleotide is N-[2-(methylthio)ethyl]-2-[(3,3,3-trifluoropropyl)thio]-5'-adenylic acid, monoanhydride with dichloromethylenebisphosphonic acid.

4. A pharmaceutical composition according to claim 1 in which the modifying additive is a polyol.

5. A pharmaceutical composition according to claim 1 in which the modifying additive is sorbitol.

6. A pharmaceutical composition according to claim 1 which further comprises 1% or more by weight of manntiol.

7. A pharmaceutical composition according to claim 1 which is in freeze-dried, spray dried or vacuum dried form.

8. A pharmaceutical composition according to claim 7 which is in reconstituted form.

9. A pharmaceutical composition according to claim 1 which is at a pH of about 6 to about 10.

10. A pharmaceutical composition according to claim 1 in which the water content is less than 5% by weight.

11. A process for the preparation of a pharmaceutical composition according to claim 7 which process comprises mixing the ingredients of the composition, and either freezing them and drying the frozen mixture, or spraying them.

12. A method of treating a platelet aggregation disorder which method comprises treating a subject suffering from a said disorder with a therapeutically effective amount of a pharmaceutical composition as defined in claim 2.

13. A process for preparing a pharmaceutical composition as defined in claim 1 which comprises mixing a nucleotide analogue, mannitol and a sodium chloride or polyol modifying additive and subjecting the mixture to a lyophilisation, vacuum drying or spray drying procedure.

* * * * *

UNITED STATES PATENT AND TRADEMARK OFFICE
CERTIFICATE OF CORRECTION

PATENT NO. : 6,114,313 C1
APPLICATION NO. : 96/000021
DATED : August 27, 2014
INVENTOR(S) : Chris Bland et al.

It is certified that error appears in the above-identified patent and that said Letters Patent is hereby corrected as shown below:

In the Claims

In claim 1, line 13, please replace "N-[2-(methlthio)ethyl]-2-[(3,3,3-trifluoropropyl)thiol]-5'-adenylic acid" with --N-[2-(methylthio)ethyl]-2-[(3,3,3-trifluoropropyl)thiol]-5'-adenylic acid--.

Signed and Sealed this
Twenty-ninth Day of September, 2015

Michelle K. Lee
*Director of the United States Patent and Trademark Office*

(12) EX PARTE REEXAMINATION CERTIFICATE (4th)
Ex Parte Reexamination Ordered under 35 U.S.C. 257

United States Patent
Bland et al.

(10) Number: US 6,114,313 C1
(45) Certificate Issued: Aug. 27, 2014

(54) PHARMACEUTICAL COMPOSITIONS FOR FREEZE DRYING

(75) Inventors: Chris Bland, Leics (GB); Gerald Steele, Leics (GB)

(73) Assignee: AstraZeneca UK Limited

Supplemental Examination Request:
No. 96/000,021, Apr. 30, 2013

Reexamination Certificate for:
Patent No.: 6,114,313
Issued: Sep. 5, 2000
Appl. No.: 09/043,159
Filed: Mar. 13, 1998

(21) Appl. No.: 96/000,021

(22) PCT Filed: Dec. 11, 1997

(86) PCT No.: PCT/SE97/02068
§ 371 (c)(1),
(2), (4) Date: Mar. 13, 1998

(87) PCT Pub. No.: WO98/28009
PCT Pub. Date: Jul. 2, 1998

(30) Foreign Application Priority Data

Dec. 20, 1996 (SE) ........................................ 9604795

(51) Int. Cl.
| | |
|---|---|
| *A61K 31/70* | (2006.01) |
| *A61K 47/26* | (2006.01) |
| *A61K 9/19* | (2006.01) |
| *A61K 9/00* | (2006.01) |
| *A61K 31/704* | (2006.01) |

(52) U.S. Cl.
CPC ............. *A61K 9/0019* (2013.01); *A61K 31/704* (2013.01); *A61K 47/26* (2013.01); *A61K 9/19* (2013.01); *Y10S 514/951* (2013.01)
USPC .................. 514/47; 514/25; 514/48; 514/53; 514/951

(58) Field of Classification Search
None
See application file for complete search history.

(56) References Cited

To view the complete listing of prior art documents cited during the supplemental examination proceeding and the resulting reexamination proceeding for Control Number 96/000,021, please refer to the USPTO's public Patent Application Information Retrieval (PAIR) system under the Display References tab.

*Primary Examiner* — Shri Ponnaluri

(57) ABSTRACT

A pharmaceutical composition comprising a nucleotide analogue, mannitol and a modifying additive which is sodium chloride or a polyol which is suitable for freeze drying.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 2, 3, 7 and 8 are cancelled.

Claims 1 and 11-13 are determined to be patentable as amended.

Claims 4-6, 9 and 10, dependent on an amended claim, are determined to be patentable.

New claims 14-17 are added and determined to be patentable.

1. A pharmaceutical composition comprising a nucleotide analog, mannitol and a modifying additive which is sodium chloride or a polyol, wherein the nucleotide *analog* is [a compound of formula]

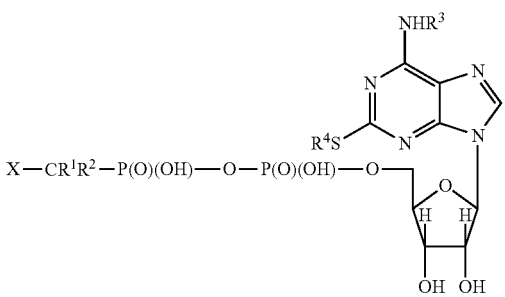

[wherein $R^1$ and $R^2$ independently represent hydrogen or halogen, $R^3$ and $R^4$ independently represent phenyl, or $C_{1-6}$-alkyl optionally substituted by one or more substituents selected from $OR^5$, $C_{1-6}$-alkylthio, $NR^6R^7$, phenyl, $COOR^8$ and halogen, $R^5$, $R^6$, $R^7$ and $R^8$ independently represent hydrogen or $C_{1-6}$-alkyl, and X represents an acidic moiety] *N-[2-(methlthio)ethyl]-2-[(3,3,3-trifluoropropyl)thio]-5'-adenylic acid, monoanhydride with dichloromethylenebisphosphonic acid, or a pharmaceutically acceptable salt thereof,*
*and wherein the pharmaceutical composition is in freeze-dried form.*

11. A process for the preparation of a pharmaceutical composition according to claim [7] *1* which process comprises mixing the ingredients of the composition, and [either] freezing them and drying the frozen mixture[, or spraying them].

12. A method of treating a platelet aggregation disorder which method comprises treating a subject suffering from a said disorder with a therapeutically effective amount of a pharmaceutical composition as defined in claim [2] *1*.

13. A process for preparing a pharmaceutical composition as defined in claim 1 which comprises mixing a nucleotide analog, mannitol and a sodium chloride or polyol modifying additive and subjecting the mixture to [a] lyophilisation[, vacuum drying or spray drying procedure], *wherein the nucleotide analog is N-[2-(methylthio)ethyl]-2-[(3,3,3-trifluoropropyl)thio]-5'-adenylic acid, monoanhydride with dichloromethylenebisphosphonic acid.*

*14. A pharmaceutical composition according to claim 1, wherein the pharmaceutical composition has total impurities less than about 1% at the time of manufacture.*

*15. A pharmaceutical composition according to claim 14, wherein the pharmaceutical composition has total impurities less than about 0.8% at the time of manufacture.*

*16. A pharmaceutical composition comprising a nucleotide analog, mannitol and sorbitol, wherein the nucleotide analog is a compound of formula*

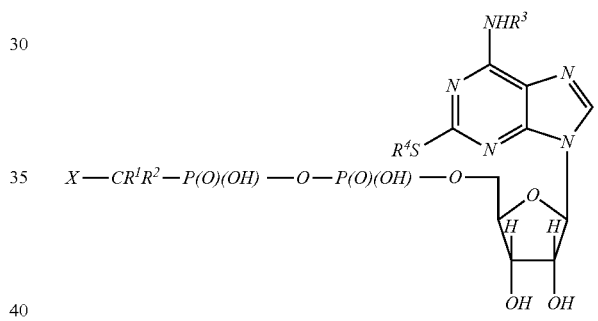

*wherein*
*$R^1$ and $R^2$ independently represent hydrogen or halogen,*
*$R^3$ and $R^4$ independently represent phenyl, or $C_{1-6}$-alkyl optionally substituted by one or more substituents selected from $OR^5$, $C_{1-6}$-alkylthio, $NR^6R^7$, phenyl, $COOR^8$ and halogen,*
*$R^5$, $R^6$, $R^7$ and $R^8$ independently represent hydrogen or $C_{1-6}$-alkyl, and*
*X represents an acidic moiety, or a pharmaceutically acceptable salt thereof.*

*17. A pharmaceutical composition according to claim 1, wherein the polyol is a straight chain polyhydric alcohol.*

* * * * *